(12) United States Patent
Ina et al.

(10) Patent No.: US 7,772,258 B2
(45) Date of Patent: Aug. 10, 2010

(54) AGENT FOR TREATMENT OF ALLERGIC EYE DISEASE

(75) Inventors: Shinji Ina, Saitama (JP); Akane Takahama, Saitama (JP)

(73) Assignee: Nikken Chemicals Co., Ltd., Chuo-ku (JP)

( * ) Notice: Subject to any disclaimer, the term of this patent is extended or adjusted under 35 U.S.C. 154(b) by 182 days.

(21) Appl. No.: 12/189,040

(22) Filed: Aug. 8, 2008

(65) Prior Publication Data

US 2008/0306163 A1 Dec. 11, 2008

Related U.S. Application Data

(63) Continuation of application No. 10/482,976, filed as application No. PCT/JP02/06912 on Jul. 8, 2002, now abandoned.

(30) Foreign Application Priority Data

Jul. 11, 2001 (JP) ............................. 2001-210239

(51) Int. Cl.
A61N 43/40 (2006.01)
A61K 31/135 (2006.01)

(52) U.S. Cl. ..................... 514/349; 514/656; 514/658

(58) Field of Classification Search .................. 514/349
See application file for complete search history.

(56) References Cited

U.S. PATENT DOCUMENTS

| 3,979,455 | A | 9/1976 | Duranleau et al. |
| 6,020,339 | A | 2/2000 | Perrier et al. |
| 6,051,718 | A | 4/2000 | Freyne et al. |
| 6,235,736 | B1 | 5/2001 | Ina et al. |

FOREIGN PATENT DOCUMENTS

| CN | 1157136 A | 8/1997 |
| EP | 0 773 024 A2 | 5/1997 |
| EP | 0 994 100 A1 | 4/2000 |
| JP | 11-189577 | 7/1999 |
| WO | WO 99/18095 | 4/1999 |

OTHER PUBLICATIONS

Office action dated Mar. 3, 2006, with English summary, for corresponding Chinese Patent Application No. 02813746.9.
Search Report for European Patent Application No. EP 02743854.8, dated Jun. 21, 2005.
Database WPI Section Ch, Week 199938, Derwent Publications Ltd., London, GB; AN 1999-452927; XP002331215 & JP 11 189577 A (Nikken Chem Co Ltd) Jul. 13, 1999; abstract.
Newsholme, Stephen J., et al., "Camp-Specific Phosphodiesterase Inhibitor, Rolipram, Reduces Eosinophil Infiltration Evoked by Leukotrienes or by Histamine in Guinea Pig Conjunctiva" Inflammation, Plenum Press, New York, NY, US, vol. 17, No. 1, Feb. 1, 1993, pp. 25-31, XP000576539; ISSN: 0360-3997.
Bourne, et al., "Modulation of Inflammation and Immunity by Cyclic AMP—Receptors for vasoactive hormones and mediators of inflammation regulate many leukocyte functions", Science, vol. 184, Apr. 5, 1974, pp. 19-28.
Abelson, et al., "Conjunctivitis of Allergic Origin: Immunologic Mechanisms and Current Approaches to Therapy", Survey of Ophthalmology, vol. 38, Supplement, Jul.-Aug. 1993 pp. 115-132, Boston, Massachusetts.
Friedlaender, "Management of ocular allergy", Review Article, Annals of Allergy, Asthma & Immunology, vol. 75, Sep. 1995, pp. 212-222, La Jolla, California.
Trophy, et al., "Novel Phosphodiesterase Inhibitors for the Therapy of Asthma", DN&P 6(4), May 1993, pp. 203-214.
Trophy, et al., "Phosphodiesterase inhibitors: new opportunities for the treatment of asthma", Thorax 1991, 46: pp. 512-523 New Drugs Review.
Revel, et al., "CR 2039, a new bis-(1H-tetrazol-5-yl) phenylbenzamide derivative with potential for the topical treatment of asthma", European Journal of Pharmacology, 229 (1992), pp. 45-53, 1992 Elsevier Science Publishers B.V. All rights reserved 0014-2999/92.
Newsholme, et al., "Camp-Specific Phosphodiesterase Inhibitor, Rolipram, Reduces Eosinophil Infiltration Evoked by Leukotrienes or by Histamine in Guinea Pig Conjunctiva", Inflammation, vol. 17, No. 1, 1993, pp. 25-31.

*Primary Examiner*—Sreeni Padmanabhan
*Assistant Examiner*—Layla Soroush
(74) *Attorney, Agent, or Firm*—Christie, Parker & Hale, LLP.

(57) ABSTRACT

An agent for the treatment of allergic eye disease containing a 3-anilino-2-cycloalkenone derivative having the formula (I):

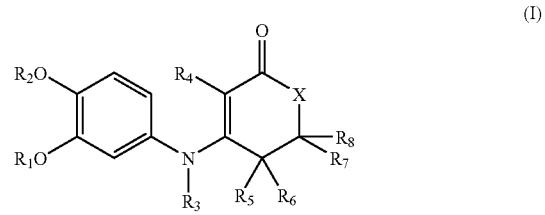

(I)

wherein $R_1$ is an unsubstituted or substituted $C_1$ to $C_8$ alkyl group provided that an unsubstituted methyl group is excluded, a $C_3$ to $C_7$ cycloalkyl group, a $C_6$ to $C_{10}$ bicycloalkyl group or an indanyl group, etc., $R_2$ is a $C_1$ to $C_4$ alkyl group, $R_3$ is a hydrogen atom, a $C_1$ to $C_5$ alkyl group, a $C_3$ to $C_7$ cycloalkyl group, etc., $R_4$ is a hydrogen atom, an unsubstituted or substituted $C_1$ to $C_5$ alkyl group, a halogen atom, etc., $R_5$, $R_6$, $R_7$ and $R_8$ are independently a hydrogen atom, a $C_1$ to $C_5$ alkyl group, etc., X is —$(CR_{11}R_{12})$n— or $NR_{13}$—, wherein n is 0 to 2, $R_{11}$, $R_{12}$ and $R_{13}$ are independently a hydrogen atom, a $C_1$ to $C_5$ alkyl group, etc.

3 Claims, No Drawings

AGENT FOR TREATMENT OF ALLERGIC EYE DISEASE

CROSS-REFERENCE TO RELATED APPLICATION(S)

This application is a continuation of patent application Ser. No. 10/482,976, filed Jan. 5, 2004, now abandoned which is the National Phase Patent Application of International Application Number PCT/JP02/06912, filed on Jul. 8, 2002, which claims priority of Japanese Patent Application Number 2001-210239, filed on Jul. 11, 2001, the entire contents of which are incorporated herein.

SUMMARY OF THE INVENTION

1. Technical Field

The present invention relates to a novel drug for the treatment of allergic eye disease effective for the treatment of allergic conjunctivitis, vernal catarrh, vernal conjunctivitis, etc. More particularly, the present invention relates to a drug for the treatment of an allergic eye disease containing a 3-anilino-2-cycloalkenone derivative having a phosphodiesterase (PDE) IV (hereinafter sometimes abbreviated as "PDE IV" in this description) inhibitory activity, or a stereoisomer or optical isomer thereof, a salt thereof, or a hydrate or solvate thereof.

2. Background Art

Allergic conjunctivitis is caused by the binding of antigens such as pollen, house dust with mast cells through antibodies (IgE). The mast cells activated by the antigens release chemical mediators such as histamines to thereby cause conjunctival injection, progression of vascular permeability and infiltration of leukocytes (eosinophils and neutrophils) and, in severe cases, to lead to tissue disorders (Abelson, M.B. et al., Surv Opthalmol 38, p. 115-132, 1993).

To treat allergic conjunctivitis, antihistamines for suppressing the action of the released histamines, sodium cromoglicate for suppressing the released of chemical mediators such as histamines, adrenocortical steroids, etc. have been used.

However, antihistamines and sodium cromoglicate cannot be expected to act to suppress the activation of free neutrophils and eosinophils, while adrenocortical steroids have the risk of causing side effects such as glaucoma, cataracts, infection, and therefore, there are limits to their use (Friedlaender M. H., Ann Allergy Asthma & Immunol. 75, p. 212-222, 1995).

From this background, development of a nonsteroidal drug possessing a clear antiinflammatory action has been desired for the treatment of allergic conjunctivitis.

In recent years, it has become clear that the activity of inflammatory cells such as neutrophils, eosinophils, mast cells is regulated by the second messenger cyclic adenosin monophosphate (cAMP) in the cells (Bourne H. R. et al, Science, 184, p. 19-28, 1974). From this fact, it has been considered that drugs increasing the intracellular concentration of cAMP would suppress inflammation. Intensive research therefor is being conducted even now.

A phosphodiesterase (PDE) IV inhibitor is expected to inhibit the cAMP hydrolyzing enzyme PDE IV present relatively commonly in inflammatory cells and raise the cAMP concentration in the cells so as to suppress the activation of the inflammatory cells, whereby an antiinflammatory activity is exhibited (Torphy, T. J. et al., Drug News Perspect, 6, p. 203-214, 1993, Torphy T. J. and Undem B. J., Thorax 46, p. 512-523, 1991).

Most PDE IV inhibitors are being developed for dealing with allergic diseases such as asthma, atopic dermatitis, rheumatoid arthritis. There are also scattered reports of using the allergic conjunctivitis model for some of these compounds (Revel, L. et al., Eur J. Pharmacol. 229, p. 45-53, 1992, Newsholme, S. J. and Schwartz, L., Inflammation 17, p. 25-31, 1993).

DETAILED DESCRIPTION OF THE INVENTION

The inventors found that a 3-anilino-2-cycloalkenone derivative having a PDE IV inhibitory activity alleviates allergic eye diseases, whereby the present invention has been completed.

That is, In accordance with the present invention, there is provided an agent for the treatment of an allergic eye disease, particularly preferably an allergic conjunctivitis treatment agent, comprising a 3-anilino-2-cycloalkenone derivative having the formula (I):

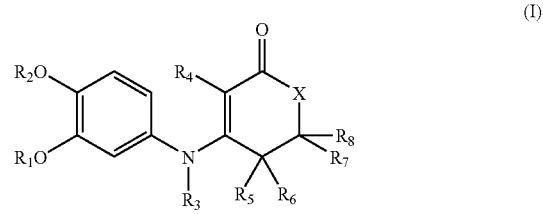

wherein $R_1$ is an unsubstituted or substituted $C_1$ to $C_8$ alkyl group provided that an unsubstituted methyl group is excluded, a $C_3$ to $C_7$ cycloalkyl group, a $C_6$ to $C_{10}$ bicycloalkyl group, a 3-tetrahydrofuryl group or an indanyl group, $R_2$ is a $C_1$ to $C_4$ alkyl group, $R_3$ is a hydrogen atom, an unsubstituted or substituted $C_1$ to $C_5$ alkyl group, a $C_3$ to $C_7$ cycloalkyl group or an acyl group, $R_4$ is a hydrogen atom, an unsubstituted or substituted $C_1$ to $C_5$ alkyl group, a halogen atom, a group having the formula (II):

wherein $R_9$ and $R_{10}$ are independently a $C_1$ to $C_5$ alkyl group, or a group having the formula (III):

wherein n is an integer of 2 to 6, provided that one $CH_2$ group may be substituted with one hetero atom selected from the group consisting of an oxygen atom, nitrogen atom and sulfur atom, $R_5$, $R_6$, $R_7$ and $R_8$ are independently a hydrogen atom, an unsubstituted or substituted $C_1$ to $C_5$ alkyl group or an unsubstituted or substituted phenyl group, X is —$(CR_{11}R_{12})_n$—, wherein $R_{11}$ and $R_{12}$ are independently a hydrogen atom, an unsubstituted or substituted $C_1$ to $C_5$ alkyl group, or an unsubstituted or substituted phenyl group, and n is an integer of 0 to 2, wherein, when n is 0, the carbonyl carbon atom adjacent to X and the other carbon atom are directly bonded to form a 5-member ring or —$NR_{13}$— wherein $R_{13}$ is a hydrogen atom or an unsubstituted or substituted $C_1$ to $C_5$ alkyl group, a stereoisomer or optical isomer thereof, a pharmacologically acceptable salt, or a hydrate or solvate thereof.

BEST MODE FOR WORKING THE INVENTION

The present invention will now be explained in detail. Note that, in the description and claims, the singular form is deemed to include the plural form unless the singular is clear from the context.

The agent for the treatment of allergic eye disease of the present invention contains one of the 3-anilino-2-cycloalkenone derivative of the above general formula (I), the stereoisomer or optical isomer thereof, the pharmacologically acceptable salt thereof, or the hydrate or solvate thereof.

As $R_1$ of the compound of the above general formula (I), a $C_1$ to $C_8$ straight chain or branched chain alkyl group (e.g., methyl, ethyl, propyl, isopropyl, n-butyl, isobutyl, sec-butyl, t-butyl, n-pentyl, 1,1-dimethylpropyl, n-hexyl, 1-methylpentyl, 1,1-dimethylbutyl, 2-ethylbutyl, n-heptyl, n-octyl, etc.) may be mentioned. These may have a substituent group (e.g., halogen atom; hydroxy group; nitro group; cyano group; amino group; carboxyl group; aryl groups such as phenyl, tolyl, naphthyl; aromatic heterocyclic group such as pyridyl, thiazolyl, thienyl, furyl, quinolyl; cycloalkyl groups such as cyclopropyl, cyclobutyl, cyclopentyl, cyclohexyl; haloalkyl group; carbamoyl group; alkoxy group; alkylcarbonyl group, etc.).

As the $C_1$ to $C_8$ alkyl group having a substituent group, for example, cyclopropylmethyl, cyclobutylmethyl, cyclopentylmethyl, cyclohexylmethyl, 1-methylcyclopropyl-methyl, 1-phenylcyclopropylmethyl, benzyl, phenethyl, 4-fluorophenethyl, 3-phenylpropyl, 4-phenylbutyl, 5-phenylpentyl, 1-naphthylmethyl, 2-naphthylmethyl, 2-(1-naphthyl)ethyl, 2-(2-naphthyl)ethyl, 2-indanylmethyl, 2-(1-naphthyl)ethyl, 2-(2-pyridyl)ethyl, 2-(4-methyl-5-thiazolyl)ethyl,2-(benzyloxy)ethyl, 2-(phenethyloxy)ethyl, 2-(methoxy)ethyl, 3-(methoxy)propyl, 4-(methoxy)butyl, 2-(ethoxy)ethyl, 3-(ethoxy)propyl, 2-(butoxyl)ethyl, 2-(cyclopropylmethyloxy)ethyl, 2-(cyclopentyloxy)ethyl, 2-(2-indanyl)ethyl, etc. may be mentioned. However, a methyl group not having a substituent group is excluded from $R_1$.

Further, as $R_1$, a $C_3$ to $C_7$ cycloalkyl group (e.g., cyclopropyl, cyclobutyl, cyclopentyl, cyclohexyl, cycloheptyl, etc.), $C_6$ to $C_{10}$ bicycloalkyl group [e.g., (1RS,2RS,4SR)bicyclo[2.2.1]hept-2-yl, (1R,2R,4S)bicyclo[2.2.1]hept-2-yl, (1S,2S,4R)bicyclo[2.2.1]hept-2-yl, etc.], 3-tetrahydrofuryl group, or indanyl group may be mentioned.

As $R_1$, preferably a $C_4$ to $C_6$ alkyl group; $C_4$ to $C_7$ cycloalkyl group; $C_6$ to $C_8$ bicycloalkyl group; $C_1$ to $C_5$ alkyl group having as a substituent group a phenyl group, naphthyl group, indanyl group, or an unsubstituted or substituted $C_3$ to $C_7$ cycloalkyl group; 3-tetrahydrofuryl group, or indanyl group may be mentioned. More preferably, cyclopentyl, cyclohexyl, cyclopropylmethyl, cyclopentylmethyl, 2-(2-indanyl)ethyl, (1RS,2RS,4SR)bicyclo [2.2.1]hept-2-yl, (1R, 2R,4S)bicyclo[2.2.1]hept-2-yl, (1S,2S,4R)bicyclo[2.2.1] hept-2-yl, or 2-indanyl may be mentioned.

As $R_2$ of the compound of the above formula (I), a $C_1$ to $C_4$ straight chain or branched chain alkyl group (e.g., methyl, ethyl, n-propyl, isopropyl, n-butyl, sec-butyl, t-butyl, etc.) may be mentioned, preferably methyl or ethyl may be mentioned, more preferably methyl may be mentioned.

As $R_3$ of the compound of the above formula (I), a hydrogen atom, a $C_1$ to $C_5$ straight chain or branched chain alkyl group (methyl, ethyl, n-propyl, isopropyl, n-butyl, sec-butyl, t-butyl, n-pentyl, etc.) may be mentioned. These may also have a substituent group (e.g., halogen atom; hydroxy group; nitro group; cyano group; amino group; carboxyl group; cycloalkyl group; haloalkyl group; carbamoyl group; alkoxy group; alkylcarbonyl group; phenyl, tolyl, naphthyl, or other aryl group; aromatic heterocyclic group containing at least one hetero atom selected from the group consisting of an oxygen atom, nitrogen atom, and sulfur atom (pyridyl, thiazolyl, furyl, thienyl, quinolyl, etc.), etc.) As the $C_1$ to $C_5$ alkyl group having a substituent group, for example, benzyl, phenethyl, 3-phenylpropyl, 4-phenylbutyl, 5-phenylpentyl, 1-naphthylmethyl, 2-naphthylmethyl, 2-pyridylmethyl, 3-pyridylmethyl, 4-pyridylmethyl, furylmethyl, thiazolylmethyl, thienylmethyl, 2-quinolylmethyl, etc. may be mentioned.

As $R_3$, a $C_3$ to $C_7$ cycloalkyl group (cyclopropyl, cyclobutyl, cyclopentyl, cyclohexyl, cycloheptyl, etc.) or acyl group (formyl, acetyl, propionyl, benzoyl, etc.) may be mentioned.

As $R_3$, preferably a hydrogen atom; $C_1$ to $C_5$ alkyl group; $C_3$ to $C_7$ cycloalkyl group; or $C_1$ to $C_2$ alkyl group having as a substituent group an aryl group or aromatic heterocyclic group containing at least one hetero atom selected from an oxygen atom, nitrogen atom, and sulfur atom may be mentioned. More preferably a hydrogen atom, methyl, propyl, pentyl, cyclopentyl, 2-pyridylmethyl, 3-pyridylmethyl, 4-pyridylmethyl, benzyl, 2-quinolylmethyl, 1-naphthylmethyl, 2-naphthylmethyl, or acetyl may be mentioned.

As $R_4$ of the compound of the above formula (I), a hydrogen atom or $C_1$ to $C_5$ straight chain or branched chain alkyl group (methyl, ethyl, propyl, isopropyl, butyl, sec-butyl, t-butyl, pentyl, etc.) may be mentioned. These may also have a substituent group (halogen atom; hydroxy group; nitro group; cyano group; amino group; carboxyl group; cycloalkyl group; haloalkyl group; carbamoyl group; alkoxy group; alkylcarbonyl group; aryl groups such as phenyl, tolyl, naphthyl; aromatic heterocyclic group containing at least one hetero atom selected from an oxygen atom, nitrogen atom and sulfur atom (e.g., pyridyl, thiazolyl, furyl, thienyl, quinolyl, etc.), etc.). Further, as $R_4$, a halogen atom (chlorine atom, bromine atom, iodine atom, etc.), a group having the following formula (II):

(II)

or the following formula (III) may be mentioned.

(III)

As $R_9$ and $R_{10}$ of the above formula (II), a $C_1$ to $C_5$ straight chain or branched chain alkyl group (e.g., methyl, ethyl, propyl, isopropyl, butyl, sec-butyl, t-butyl, pentyl, etc.) may be independently mentioned, while as specific examples of the group of the above general formula (II), 1-azetidinylmethyl, 1-pyrrolidinylmethyl, 1-piperidylmethyl, 1-homo-piperidylmethyl, 1-piperazinylmethyl, morpholinomethyl, etc. may be mentioned.

The n of the above formula (III) is an integer of 2 to 6. Further, one $CH_2$ group may be substituted with one hetero atom selected from an oxygen atom, nitrogen atom and sulfur atom.

As $R_4$, preferably a hydrogen atom, halogen atom, $C_1$ to $C_3$ alkyl group, dimethylaminomethyl, morpholinomethyl, or benzyl may be mentioned.

As $R_5$, $R_6$, $R_7$ and $R_8$ of the above formula (I), a hydrogen atom, $C_1$ to $C_5$ straight chain or branched chain alkyl group (methyl, ethyl, propyl, isopropyl, butyl, sec-butyl, t-butyl, pentyl, etc.), phenyl group, etc. may be independently mentioned. The $C_1$ to $C_5$ alkyl group and phenyl group may also have a substituent group (e.g., halogen atom; hydroxy group; nitro group; cyano group; amino group; carboxyl group; alkyl group; cycloalkyl group; haloalkyl group; carbamoyl group; alkoxy group; alkylcarbonyl group; aryl groups such as phenyl, tolyl, naphthyl; aromatic heterocyclic group containing at least one hetero atom selected from an oxygen atom, nitrogen atom, and sulfur atom (e.g., pyridyl, thiazolyl, furyl, thienyl, quinolyl, etc.), etc.) As $R_5$, $R_6$, $R_7$ and $R_8$, a hydrogen atom or methyl may be preferably mentioned.

As the X of the above formula (I), $-(CR_{11}R_{12})_n-$ wherein $R_{11}$ and $R_{12}$ are independently a hydrogen atom, substitutable $C_1$ to $C_5$ alkyl group, or an unsubstituted or substituted phenyl group, and n is an integer of 0 to 2, where when n is 0, the carbonyl carbon atom adjacent to X and the other carbon atom are directly bonded to form a 5-member ring or $-NR_{13}-$ wherein, as $R_{13}$, a hydrogen atom or $C_1$ to $C_5$ straight chain or branched chain alkyl group (e.g., methyl, ethyl, propyl, isopropyl, butyl, sec-butyl, t-butyl, pentyl, etc.) may be mentioned and may have a substituent group (e.g., halogen atom; hydroxy group; nitro group; cyano group; amino group; carboxyl group; cycloalkyl group; haloalkyl group; carbamoyl group; alkoxy group; alkylcarbonyl group; aryl group such as phenyl, tolyl, naphthyl; aromatic heterocyclic group containing at least one hetero atom selected from an oxygen atom, nitrogen atom and sulfur atom (e.g., pyridyl, thiazolyl, furyl, thienyl, quinolyl, etc.), etc.). As examples of an alkyl group having a substituent group, benzyl, phenethyl, 3-phenylpropyl, 4-phenylbutyl, 5-phenylpentyl, pyridylmethyl, furylmethyl, and thiazolylmethyl may be mentioned. As X, preferably, $-(CR_{11}R_{12})_n-$ where n is 0 or 1, wherein, when n is 1, $R_{11}$ and $R_{12}$ preferably are independently a hydrogen atom or methyl group or $-NR_{13}-$ wherein $R_{13}$ is a hydrogen atom, $C_1$ to $C_3$ alkyl group or benzyl group may be mentioned.

As specific examples of the compound of the above formula (I), 3-(3-cyclopentyloxy-4-methoxyanilino)-2-cyclopenten-1-one, 3-(3-cyclopentyloxy-4-methoxyanilino)-2-cyclohexen-1-one, 3-(3-cyclopentyloxy-4-methoxyanilino)-5,5-dimethyl-2-cyclohexen-1-one, 3-(3-cyclopentyloxy-4-methoxyanilino)-2-methyl-2-cyclopenten-1-one, 3-(3-cyclopentyloxy-4-methoxyanilino)-5-methyl-2-cyclohexen-1-one, 2-chloro-3-(3-cyclopentyloxy-4-methoxyanilino)-2-cyclopenten-1-one, 2-bromo-3-(3-cyclopentyloxy-4-methoxyanilino)-2-cyclopenten-1-one, 3-[3-[(1RS,2RS,4SR)-bicyclo[2.2.1]hept-2-yloxy]-4-methoxyanilino]-2-cyclopenten-1-one, 3-[3-(2-indanyloxy)-4-methoxyanilino]-2-cyclopenten-1-one, 3-[3-(2-indanyloxy)-4-methoxyanilino]-2-methyl-2-cyclopenten-1-one, 3-(4-methoxy-3-phenethyloxyanilino)-2-cyclopenten-1-one, 3-(4-methoxy-3-phenethyloxyanilino)-2-methyl-2-cyclopenten-1-one, 3-(3-cyclohexyloxy-4-methoxyanilino)-2-cyclopenten-1-one, 3-(3-cyclohexyloxy-4-methoxyanilino)-2-methyl-2-cyclopenten-1-one, 3-(3-cyclopropylmethoxy-4-methoxyanilino)-2-cyclopenten-1-one, 3-(3-cyclopropylmethoxy-4-methoxyanilino)-2-methyl-2-cyclopenten-1-one, 3-(3-butoxyl-4-methoxyanilino)-2-cyclopenten-1-one, 3-(3-butoxyl-4-methoxyanilino)-2-methyl-2-cyclopenten-1-one, 3-[3-(2-indanyloxy)-4-methoxyanilino]-2-cyclohexen-1-one, 3-(3-benzyloxy-4-methoxyanilino)-2-cyclohexen-1-one, 4-(3-cyclopentyloxy-4-methoxyanilino)-1,2,5,6-tetrahydropyridin-2-one, 1-benzyl-4-(3-cyclopentyloxy-4-methoxyanilino)-1,2,5,6-tetrahydropyridin-2-one, 4-[3-[3-[(1RS,2RS,4SR)-bicyclo[2.2.1]hept-2-yloxy]-4-methoxyanilino]-1,2,5,6-tetrahydropyridin-2-one, 3-(3-cyclopentyloxy-4-methoxyanilino)-2-dimethylaminomethyl-2-cyclopenten-1-one, 3-(3-cyclopentyloxy-4-methoxyanilino)-2-(4-morpholinomethyl)-2-cyclopenten-1-one, 3-(3-cyclopentyloxy-4-methoxy-N-methylanilino)-2-cyclopenten-1-one, 3-(3-cyclopentyloxy-4-methoxy-N-methylanilino)-2-cyclohexen-1-one, 3-[3-cyclopentyloxy-4-methoxy-N-(4-pyridylmethyl)anilino]-2-cyclopenten-1-one, 3-(N-acetyl-3-cyclopentyloxy-4-methoxyanilino)-2-cyclopenten-1-one, 3-(N-benzyl-3-cyclopentyloxy-4-methoxyanilino)-2-cyclopenten-1-one, 3-(3-cyclopentyloxy-4-methoxyanilino)-2-ethyl-2-cyclopenten-1-one, 2-ethyl-3-[3-(2-indanyloxy)-4-methoxyanilino]-2-cyclopenten-1-one, 2-benzyl-3-(3-cyclopentyloxy-4-methoxyanilino)-2-cyclopenten-1-one, 3-[3-[2-(2-indanyl)ethoxy]-4-methoxyanilino]-2-cyclopenten-1-one, 3-[3-[2-(2-indanyl)ethoxy]-4-methoxyanilino]-2-methyl-2-cyclopenten-1-one, 3-[4-methoxy-3-(2,3,4,5-tetrahydrofuran-3-yloxy)anilino]-2-cyclopenten-1-one, 3-[4-methoxy-3-(2,3,4,5-tetrahydrofuran-3-yloxy)anilino]-2-methyl-2-cyclopenten-1-one, 3-(3-cyclopentyloxy-4-methoxyanilino)-6,6-dimethyl-2-cyclohexen-1-one, 3-(3-cyclopentyloxy-4-methoxyanilino)-5-phenyl-2-cyclohexen-1-one, 3-(3-cyclopentylmethoxy-4-methoxyanilino)-2-cyclopenten-1-one, 3-(3-cyclopentylmethoxy-4-methoxyanilino)-2-methyl-2-cyclopenten-1-one, 3-[4-methoxy-3-[2-(1-naphthyl)ethoxy]anilino]-2-cyclopenten-1-one, 3-[4-methoxy-3-[2-(1-naphthyl)ethoxy]anilino]-2-methyl-2-cyclopenten-1-one, 3-[3-[(1RS,2RS,4SR)-bicyclo[2.2.1]hept-2-yloxy]-4-methoxyanilino]-2-methyl-2-cyclopenten-1-one, 3-[3-[(1RS,2RS,4SR)-bicyclo[2.2.1]hept-2-yloxy]-4-methoxyanilino]-2-ethyl-2-cyclopenten-1-one, 3-[3-[(1RS,2RS,4SR)-bicyclo[2.2.1]hept-2-yloxy]-4-methoxyanilino]-2-methyl-2-cyclohexen-1-one, 3-[3-[(1RS,2RS,4SR)-bicyclo[2.2.1]hept-2-yloxy]-4-methoxy-N-methylanilino]-2-methyl-2-cyclopenten-1-one, 3-[3-(2-indanyloxy)-4-methoxyanilino]-2-methyl-2-cyclohexen-1-one, 3-[4-methoxy-3-[(1-phenylcyclopropyl)methoxy]anilino]-2-cyclopenten-1-one, 3-[4-methoxy-3-[(1-phenylcyclopropyl)methoxy]anilino]-2-methyl-2-cyclopenten-1-one, 3-(3-cyclobutylmethoxy-4-methoxyanilino)-2-cyclopenten-1-one, 3-(3-cyclobutylmethoxy-4-methoxyanilino)-2-methyl-2-cyclopenten-1-one, 3-[3-[2-(2-indanyl)ethoxy]-4-methoxyanilino]-2-methyl-2-cyclohexen-1-one, 3-(3-cyclopentylmethoxy-4-methoxyanilino)-2-methyl-2-cyclohexen-1-one, 3-(3-cyclohexyloxy-4-methoxyanilino)-2-methyl-2-cyclohexen-1-one, 3-(N-benzyl-3-cyclohexyloxy-4-methoxyanilino)-2-cyclopenten-1-one, 3-[3-cyclohexyloxy-4-methoxy-N-(2-naphthylmethyl)anilino]-2-cyclopenten-1-one, 3-[3-cyclopentyloxy-4-methoxy-N-(2-quinolylmethyl)anilino]-2-cyclopenten-1-one, 3-(3-cyclopentyloxy-4-methoxy-N-propylanilino)-2-cyclopenten-1-one, 3-(N-cyclopentyl-3-cyclopentyloxy-4-methoxyanilino)-2-cyclopenten-1-one, 3-[3-cyclopentyloxy-4-methoxy-N-(2-pyridylmethyl)anilino]-2-cyclopenten-1-one, 3-[3-cyclopentyloxy-4-methoxy-N-(2-naphthylmethyl) anilino]-2-cyclopenten-1-one, 3-[3-cyclopentyloxy-4-methoxy-N-(3-pyridylmethyl)anilino]-2-cyclopenten-1-one, 3-(3-cyclopentyloxy-4-methoxy-N-pentylanilino)-2-cyclopenten-1-one, 3-[3-(2-indanyloxy)-4-methoxy-N-methylanilino]-2-cyclohexen-1-one, 3-[N-benzyl-3-(2-indanyloxy)-4-methoxyanilino]-2-cyclohexen-1-one, 3-[3-(2-indanyloxy)-4-methoxy-N-(2-naphthylmethyl)anilino]-2-cyclohexen-1-one, 3-[3-(2-indanyloxy)-4-methoxy-N-(2-pyridylmethyl)anilino]-2-cyclohexen-1-one, 2-benzyl-3-(3-cyclopentyloxy-4-methoxyanilino)-2-cyclohexen-1-one, 3-(3-cyclopentyloxy-4-methoxy-N-methylanilino)-2-methyl-2-cyclopenten-1-one, 3-(N-benzyl-3-cyclopentyloxy-4-methoxyanilino)-2-methyl-2-cyclopenten-1-one, 3-[3-cyclopentyloxy-4-methoxy-N-(2-quinolylmethyl)anilino]-2-methyl-2-cyclopenten-1-one, 3-[3-(2-indanyloxy)-4-methoxy-N-(4-pyridylmethyl)anilino]-2-methyl-2-cyclopenten-1-one, 3-[3-(2-indanyloxy)-4-methoxy-N-(2-naphthylmethyl)anilino]-2-methyl-2-cyclopenten-1-one, 3-(3-cyclopentyloxy-4-methoxyanilino)-2-methyl-2-cyclohexen-1-one, 3-[3-(2-indanyloxy)-4-methoxy-N-methylanilino]-2-cyclopenten-1-one, 3-[N-benzyl-3-(2-indanyloxy)-4-methoxyanilino]-2-cyclopenten-1-one, 3-[3-(2-indanyloxy)-4-methoxy-N-(4-pyridylmethyl)anilino]-2-cyclopenten-1-one, 3-[3-(2-indanyloxy)-4-methoxy-N-(2-naphthylmethyl)anilino]-2-cyclopenten-1-one, 3-[3-(2-indanyloxy)-4-methoxy-N-(2-quinolylmethyl)anilino]-2-cyclopenten-1-one, 3-[N-benzyl-3-[(1RS,2RS,4SR)-bicyclo[2.2.1]hept-2-yloxy]-4-methoxyanilino]-2-cyclopenten-1-one, 3-[3-[(1RS,2RS,4SR)-bicyclo[2.2.1]hept-2-yloxy]-4-methoxy-N-(2-quinolylmethyl)anilino]-2-cyclopenten-1-one, 3-[3-[(1RS,2RS,4SR)-bicyclo[2.2.1]hept-2-yloxy]-4-methoxyanilino]-2-cyclohexen-1-one, 3-[N-benzyl-3-[(1RS,2RS,4SR)-bicyclo[2.2.1]hept-2-yloxy]-4-methoxyanilino]-2-cyclohexen-1-one, 3-[3-[(1RS,2RS,4SR)-bicyclo[2.2.1]hept-2-yloxy]-4-methoxy-N-(4-pyridylmethyl)anilino]-2-cyclohexen-1-one, (−)-3-[3-[(1R,2R,4S)-bicyclo[2.2.1]hept-2-yloxy]-4-methoxyanilino]-2-methyl-2-cyclopenten-1-one, (+)-3-[3-[(1S,2S,4R)-bicyclo[2.2.1]hept-2-yloxy]-4-methoxyanilino]-2-methyl-2-cyclopenten-1-one, etc. may be mentioned.

The 3-anilino-2-cycloalkenone derivative of the above formula (I) may be produced by the method described in, for example, Japanese Unexamined Patent Publication (Kokai) No. 11-189577.

Further, the 3-anilino-2-cycloalkenone derivative of the above formula (I) has asymmetric carbon atoms and, therefore, has optical isomers. These optically pure compounds are obtained by dividing the racemate produced by the method described in the above publication into the optical isomers using high pressure liquid chromatography (HPLC). By recrystallizing the obtained optical isomers when needed, further higher purity optical isomers can be obtained. These optical isomers are also considered to be included in the content of the agent for the treatment of the allergic eye disease of the present invention.

Further, the salts of the compound of the above formula (I) and the stereoisomer or optical isomer thereof are also included in the content of the agent for the treatment of the allergic eye disease of the present invention. As these salts, pharmacologically acceptable salts are preferable. For example, inorganic acid salts such as hydrochlorate, hydrobromate, hydroiodate, phosphate; and organic acid salts such as oxalate, maleate, fumarate, lactate, malate, citrate, tartarate, benzoate, methanesulfonate, p-toluenesulfonate may be mentioned.

Further, the agent for the treatment of allergic eye disease of the present invention may also include hydrates or solvates of the 3-anilino-2-cycloalkenone derivative of the above formula (I), its stereoisomer or optical isomer, or their salts. As the solvent of the solvate, methanol, ethanol, isopropanol, butanol, acetone, ethyl acetate, chloroform, etc. may be mentioned.

The agent for the treatment of allergic eye disease of the present invention may be produced by preparing the 3-anilino-2-cycloalkenone derivative of the above formula (I), its stereoisomer or optical isomer, their pharmaceutically allowable salts, or their hydrates or solvates, alone or mixed with a pharmacologically acceptable vehicle, into a suitable unit form of administration. The composition thereof is determined depending upon the solubility of the compound, the chemical properties, route of administration, the plan of administration, etc.

As examples of the form of administration, in the case of topical administration, an eye drop, eye ointment, etc. or, in the case of systemic administration, tablets, granules, a dispersion, capsules, a liquid, injection, etc. may be mentioned. In particular, the agent for the treatment of allergic eye disease of the present invention is preferably used in the form of an eye drop.

The agent for the treatment of allergic eye disease of the present invention is produced by any method known to persons skilled in the art, using the 3-anilino-2-cycloalkenone derivative of the above formula (I), its optical isomer, their pharmacologically acceptable salts, or their hydrates or solvates and a pharmacologically acceptable vehicle.

Further, as desired or when needed, it is also possible to add various additives usually used when making a preparation such as a suitable binder, lubricant, disintegrant, preservative, buffer, thickener, solution adjuvant, chelating agent, stabilizer, pH adjuster, or isotonic agent.

For example, in the case of an oral drug, excipients such as lactose, crystalline cellulose, glucose, corn starch, sucrose, sorbitol, erythritol; disintegrants such as calcium carboxymethylcellulose, hydroxypropylcellulose; lubricants such as calcium stearate, magnesium stearate, talc, polyethylene glycol, hydrogenated oil, or another gloss agent, hermectants such as hydroxypropylcellulose, hydroxypropylmethyl-cellulose, carboxymethylcellulose, polyvinylalcohol, gelatin, gum arabic, and also when needed a surfactant, flavoring agents, etc. may be used to prepare the desired form of administration.

Further, in the case of a non-oral drug, a dilvents such as water, ethanol, glycerin, propyleneglycol, polyethyleneglycol, agar, gum tragacanth may be used, when needed, solution adjuvants (e.g., polyvinylpyrrolidone, polyoxyethylene hydrogenated castor oil, polyethylene glycol, Polysorbate 80, polyoxyethylene monostearate, etc.), preservative (chlorobutanol, sodium dehydroacetate, benzalkonium chloride, cetylpyridium chloride, phenethyl alcohol, p-oxybenzoate esters, benzethonium chloride, etc.), buffer (borate buffer, phosphate buffer, carbonate buffer, acetate buffer, citrate buffer, etc.), stabilizer (sodium edetate, sodium hydrogensulfite, etc.), pH adjuster (sodium hydroxide, potassium hydroxide, sodium carbonate, sodium bicarbonate, acetic acid, citric acid, phosphoric acid, etc.), isotonic agent (sodium chloride, potassium chloride, glycerin, polyhydric alcohol, sorbitol, mannitol, glucose, etc.), soothing agents, etc. may be used.

In the case of an eye ointment, a normally used base (ophthamalic white vaseline, plastibase, propeto, etc.) may be used, while as an additive, liquid paraffin etc. may be mentioned.

The compound of the above formula (I) usable in the present invention is usually used at a concentration of 0.01 to 3.0 w/v % in the case of an eye drop and is usually used at a concentration of 0.01 to 10.0 w/v % in the case of an eye ointment. Further, when used as a preparation for systemic administration, the dosage, in the case of oral administration, is generally 0.01 to 1000 mg per day, preferably 0.01 to 100 mg per day, but the dosage is more preferably adjusted according to age, condition, symptoms, existence of co-administration, etc.

The clinical usage and dosage of the agent for the treatment of allergic eye disease of the present invention changes depending on the age, condition, symptoms, etc., but in the case of an eye drop, usually one to two drops are applied from one to six times a day. In the case of an eye ointment, usually a suitable quantity is applied to the conjunctival sac one to two times a day. In the case of oral administration, the dosage is ingested once a day or divided into several times. Further, in the case of an injection, it is injected once a day or divided into several times.

EXAMPLES

The present invention will now be described in detail by examples and a test example, but the present invention is not limited to these Examples and Test.

Reference Example 1

Method of Production of Optical Isomer 1.8 g of the racemic mixture (±)-3-[3-[(1RS,2RS,4SR)-bicyclo[2.2.1]hept-2-yloxy]-4-methoxyanilino]-2-methyl-2-cyclopenten-1-one 1 produced by the method described in Japanese Unexamined Patent Publication (Kokai) No. 11-189577 was dissolved in 1.8 L of a mobile phase, then about 70 mg of the sample solution was injected into a column all at once for HPLC.

Column: CHIRALCEL OD (10 cmφ×50 cm)

Mobile phase: n-hexane/isopropanol/diethylamine=90/10/0.1

Flow rate: 190 mL/min

The fractions of the first peak and the second peak were concentrated in vacuo to obtain an oily residue. Ethanol and n-hexane were added to this, then the mixture was again concentrated in vacuo to obtain powdery optical isomers. The above operation was repeated to obtain from the 1.8 g of the (±)-3-[3-[(1RS,2RS,4SR)-bicyclo[2.2.1]hept-2-yloxy]-4-methoxyanilino]-2-methyl-2-cyclopenten-1-one two types of optical isomers, that is, the (−)-isomer and (+)-isomer, in amounts of 0.70 g and 0.64 g. Further, the structures of the optical isomers were confirmed by comparison with the racemate $^1$H-NMR.

(−)-isomer: retention time 86 to 98 min, column temperature 40° C.

$[\alpha]^{20}_D$-19° (c=1.00, EtOH)

$^1$H-NMR (400 MHz, CDCl$_3$) δ(ppm): 1.12-1.18(2H, m), 1.21-1.23(1H, m), 1.48-1.54(1H, m), 1.56-1.64(2H, m), 1.68 (3H, s), 1.72-1.80(2H, m), 2.35(1H, m), 2.39-2.41(2H, m), 2.51(1H,d,J=4.39 Hz), 2.55-2.56(2H, m), 3.85(3H, s), 4.16-4.17(1H, m), 6.41(1H,broad s), 6.65(1H,d,J=2.44 Hz), 6.69 (1H,dd,J=8.79, 2.44 Hz), 6.83(1H,d,J=8.79 Hz)

(+)-isomer: retention time 103 to 121 min, column temperature 40° C.

$[\alpha]^{20}_D$+19°(c=1.00, EtOH)

(±)-isomer $^1$H-NMR(400 MHz, CDCl$_3$) δ (ppm):
1.12-1.18(2H, m), 1.21-1.23(1H, m), 1.48-1.54(1H, m), 1.56-1.64(2H, m), 1.68(3H, s), 1.72-1.80(2H, m), 2.35(1H, m), 2.39-2.41(2H, m), 2.51(1H,d,J=4.39 Hz), 2.55-2.56(2H, m), 3.85 (3H, s), 4.16-4.17(1H, m), 6.47(1H,broad s), 6.65 (1H,d,J=2.44 Hz), 6.69(1H,dd,J=8.79, 2.44 Hz), 6.83(1H,d, J=8.79 Hz)

Example 1

Production of Eye Prop

To sterile water, methylcellulose in an amount of 0.3 g, benzalkonium chloride solution in a small amount, sodium dihydrogenphosphate in an amount of 0.2 g, and sodium hydroxide in a suitable quantity were added and dissolved and then the mixture was filtered to remove dust and bacteria. Dirt- and bacteria-free 3-[3-cyclopentyloxy-4-methoxy-N-(2-naphthylmethyl)anilino]-2-cyclopenten-1-one in an amount of 0.5 g was suspended in this solution, then sterile water was added to give a total volume of 100 mL. The suspension thus obtained was filled in a certain amount in a washed, dried, and sterilized eye drop container and a nozzle and cap attached to prepare the eye drop.

Example 2

Production of Eye Ointment 0.5 g of 3-[3-cyclopentyloxy-4-methoxy-N-(2-naphthylmethyl)anilino]-2-cyclopenten-1-one, 10.0 g of refined lanolin, 80.0 g of ophthalmic white vaseline and 0.5 g of liquid paraffin were taken and adjusted to a total weight 100.0 g to prepare an ointment by the method of production of an eye ointment.

Test Example 1

Alleviating Action for Allergenic Conjunctivitis Model or the experiment, Wistar rats (CLEA Japan) were used. The rats were sensitized by intraperitoneal administration of ovalbumin (OA, made by Sigma) in an amount of 100 μg and 10 mg of aluminum hydroxide (Alum, made by Pierce Co.) suspended in 1 mL of physiological saline. Allergic conjunctivitis was induced using rats after 3 weeks from the date of sensitization by dropping into the eyes of 10 μg OA solution prepared by physiological saline to a concentration of 30 mg/mL. The medicine was suspended at a concentration of 1.0 w/v % in physiological saline and dropped into the eyes 10 minutes before OA challenge to induce conjunctivitis (as a positive control drug, diphenhydramine suspended in a concentration of 0.3 w/v % in physiological saline was dropped in the eyes 10 minutes before OA challenge to induce conjunctivitis).

For the effect of the compound, the number of times of the action of using the hind legs to scratch the eye area (Itch-Scratch response; considered to be an indicator of itchiness) observed in the 20-minute period after dropping the OA was counted and used to find the rate of inhibition of itchiness by the following formula:

Control group: presensitized rats in whose eyes physiological saline is dropped 10 minutes before using OA to induce conjunctivitis Untreated group: unsensitized rats in whose eyes physiological saline is dropped.

Calculation Formula:

Inhibition rate(%)=100−(test substance group−untreated group/(control group−untreated group)×100

Table I shows the results when using for the test substance 3-[3-cyclopentyloxy-4-methoxy-N-(2-naphthylmethyl)anilino]-2-cyclopenten-1-one (compound 1), 3-[3-[(1RS,2RS,4SR)-bicyclo[2.2.1]hept-2-yloxy]-4-methoxyanilino]-2-methyl-2-cyclopenten-1-one (compound 2), 3-[3-[(1RS,2RS,4SR)-bicyclo[2.2.1]hept-2-yloxy]-4-methoxyanilino]-2-ethyl-2-cyclopenten-1-one (compound 3), (−)-3-[3-[(1R,2R,4S)-bicyclo[2.2.1]hept-2-yloxy]-4-methoxyanilino]-2-methyl-2-cyclopenten-1-one (compound 4), and (+)-3-[3-[(1S,2S,4R)-bicyclo[2.2.1]hept-2-yloxy]-4-methoxyanilino]-2-methyl-2-cyclopenten-1-one (compound 5).

TABLE I

Alleviating Activity for Allergic Conjunctivitis Model

| Test substance | No. of animal | Inhibition rate (%) |
|---|---|---|
| Compound 1 | 5 | 82.7 |
| Compound 2 | 5 | 62.9 |
| Compound 3 | 5 | 63.5 |
| Compound 4 | 5 | 68.6 |
| Compound 5 | 5 | 97.1 |
| Diphenhydramine | 5 | 64.6 |

As a result, with the eye drops of 1.0 w/v % of the above compounds 1 to 5, an effect of inhibition of the Itch-Scratch response equal to, or greater than, that of the positive control diphenhydramine was observed. It was considered that the edema and itchiness of the eyes appearing in the allergic conjunctivitis model were inhibited.

Further, with the nontreated group where physiological saline was dropped into the eye, no edema was observed and an Itch-Scratch Response was observed once in one animal out of the four. This is believed to have been induced by the physical stimulus due to the dropping in the eye. In the control group dropping OA into the eye, light to medium edema and Itch-Scratch response was observed in all animal. It was considered that acute allergic conjunctivitis was induced.

INDUSTRIAL APPLICABILITY

The agent for the treatment of allergic eye disease of the present invention contains a compound having an activity different from that of existing the agent for the treatment of allergic eye disease (PDE IV inhibitory activity), whereby, a good effect of alleviating allergic conjunctivitis can be obtained and therefore is extremely useful as a new type agent for the treatment of allergic eye disease.

What is claimed is:

1. A method for treating a conjunctivitis eye disease comprising administering a medicament comprising a compound selected from the group consisting of (+)-3-[3-[(1S,2S,4R)-bicyclo[2.2.1]hept-2-yloxy]-4-methoxyanilino]-2-methyl-2-cyclopenten-1-one, and a pharmacologically acceptable salt thereof.

2. A method as claimed in claim 1, wherein the medicament further comprises a carrier suitable for topical administration.

3. A method as claimed in claim 2, wherein the carrier is suitable for use as an eye drop.

* * * * *